United States Patent
Jensen et al.

(10) Patent No.: US 11,432,714 B2
(45) Date of Patent: Sep. 6, 2022

(54) METHOD FOR MANUFACTURE OF A TIP PART AND A TIP PART FOR AN ENDOSCOPE

(71) Applicant: AMBU A/S, Ballerup (DK)

(72) Inventors: Thomas Bachgaard Jensen, Copenhagen (DK); Rung De Lin, Taichung (TW)

(73) Assignee: AMBU A/S, Ballerup (DK)

( * ) Notice: Subject to any disclaimer, the term of this patent is extended or adjusted under 35 U.S.C. 154(b) by 291 days.

(21) Appl. No.: 16/584,557

(22) Filed: Sep. 26, 2019

(65) Prior Publication Data

US 2020/0100663 A1 Apr. 2, 2020

(30) Foreign Application Priority Data

Sep. 28, 2018 (EP) .................... 18197491

(51) Int. Cl.
  *A61B 1/00* (2006.01)
  *A61B 1/05* (2006.01)
  *A61B 1/005* (2006.01)

(52) U.S. Cl.
  CPC .............. *A61B 1/051* (2013.01); *A61B 1/005* (2013.01); *A61B 1/0011* (2013.01); *A61B 1/00045* (2013.01); *A61B 1/00096* (2013.01)

(58) Field of Classification Search
  CPC ............ A61B 1/0011; A61B 1/05–051; A61B 1/00096; H04N 2005/2255; H04N 5/2253;

(Continued)

(56) References Cited

U.S. PATENT DOCUMENTS 4,998,916 A 3/1991 Hammerslag et al.
8,790,250 B2 7/2014 Petersen et al.
(Continued)

FOREIGN PATENT DOCUMENTS

JP 2004008638 A 1/2004
JP 2009279182 A 12/2009
(Continued)

OTHER PUBLICATIONS

Extended Search Report dated Apr. 5, 2019 in corresponding European Application No. 18197491, all pages.

*Primary Examiner* — Alexandra L Newton
(74) *Attorney, Agent, or Firm* — Faegre Drinker Biddle & Reath LLP

(57) ABSTRACT

A method for manufacture of a tip part for an endoscope including providing a camera assembly, an exterior housing including a circumferential wall enclosing a spacing and a distal end wall integral with the circumferential wall and having an opening; inserting a lens barrel of the camera assembly in the spacing so that a distal end of the lens barrel of the camera assembly extends into the opening, and so that an axially extending adhesive spacing is provided between the opening and the lens barrel along a circumference of the lens barrel, a radial extent of the adhesive spacing gradually being reduced in a direction towards the spacing of the exterior housing; injecting an adhesive into the adhesive spacing; and allowing or causing the adhesive to harden so as to adhere the lens barrel to the distal end wall of the exterior housing.

20 Claims, 6 Drawing Sheets

(58) Field of Classification Search
CPC .. H04N 5/2254; H04N 5/2251; H04N 5/2252; G02B 23/2484; G02B 23/2423
See application file for complete search history.

(56) References Cited

U.S. PATENT DOCUMENTS

| | | |
|---|---|---|
| 9,220,400 B2 | 12/2015 | Petersen |
| 10,321,804 B2 | 6/2019 | Jacobsen et al. |
| 2002/0193663 A1 | 12/2002 | Matsuura |
| 2008/0242935 A1 | 10/2008 | Inoue |
| 2008/0266441 A1* | 10/2008 | Ichimura .............. H04N 5/2254 348/340 |
| 2013/0041223 A1 | 2/2013 | Kato |
| 2013/0090529 A1 | 4/2013 | Boulais |
| 2014/0210976 A1 | 7/2014 | Lin |
| 2016/0051222 A1 | 2/2016 | Imahashi |
| 2017/0020365 A1* | 1/2017 | Hamazaki .......... A61B 1/00002 |
| 2018/0078127 A1* | 3/2018 | Igarashi ............. G02B 23/2469 |
| 2018/0242822 A1* | 8/2018 | Hamazaki ............ A61B 1/0011 |
| 2019/0175007 A1 | 6/2019 | Sorensen et al. |
| 2019/0191968 A1* | 6/2019 | Tsumaru ............ A61B 1/00062 |

FOREIGN PATENT DOCUMENTS

| | | |
|---|---|---|
| JP | 2010005277 A | 1/2010 |
| JP | 2011200399 A | 10/2011 |
| JP | 2015058118 A | 3/2015 |
| KR | 20160056725 A | 5/2016 |
| WO | WO 2010/066790 A1 | 6/2010 |
| WO | WO 2014/106511 A1 | 7/2014 |
| WO | WO 2016/188543 A1 | 12/2016 |

\* cited by examiner

METHOD FOR MANUFACTURE OF A TIP PART AND A TIP PART FOR AN ENDOSCOPE

CROSS-REFERENCE TO RELATED APPLICATIONS

This application claims priority from European Patent Application No. 18197491, filed Sep. 28, 2018, which application is incorporated herein by reference thereto.

TECHNICAL FIELD

The present disclosure relates to endoscopes, and more specifically to a tip part for an endoscope.

BACKGROUND

Endosopes are well known for visually inspecting inaccessible places such as human body cavities. Typically, the endoscope comprises an elongated insertion tube with a handle at the proximal end, as seen from the operator, and visual inspection means, such as a built-in camera, at the distal end of the elongated insertion tube. This definition of the terms distal and proximal, i.e. proximal being the end closest to the operator and distal being the end remote from the operator, as used herein for endoscopes in general, is adhered to in the present specification.

As the name indicates, endoscopes are used for seeing inside things, such as lungs or other human body cavities of a patient. Modern endoscopes are therefore typically equipped with a light source and a vision receptor including a vision sensor, such as a camera or an image sensor. Provided that sufficient light is present, it is possible for the operator to see where the endoscope is steered and to set the target of interest once the tip has been advanced thereto. This therefore normally requires illumination of the area in front of the distal tip of the endoscope, in particular the field of vision of the camera(s). The light source, such as a light emitting diode or an optical fibre, may provide illumination.

Electrical wiring for the camera and other electronics, such as LED lighting accommodated in the tip part at the distal end, run along the inside of the elongated insertion tube from the handle to the tip part. Instead of using cameras, endoscopes may also be fibre-optic, in which case the optical fibres run along the inside of the elongated insertion tube to the tip part. For some applications, a working or suction channel may run along the inside of the insertion tube from the handle to the tip part, e.g. allowing liquid to be removed from the body cavity or allowing for insertion of surgical instruments or the like, into the body cavity. The suction channel may be connected to a suction connector, typically positioned at a handle at the proximal end of the insertion tube. For other applications, the working or suction channel may be omitted.

In order to be able to manoeuvre the endoscope inside the body cavity, the distal end of the endoscope may comprise a bending section with increased flexibility, e.g. an articulated tip part allowing the operator to bend this section. Typically, this is done by tensioning or slacking steering wires also running along the inside of the elongated insertion tube from the articulated tip part to a control mechanism of the handle. Furthermore, a working channel may run along the inside of the insertion tube from the handle to the tip, e.g. allowing liquid to be removed from the body cavity or allowing the insertion of surgical instruments or the like into the body cavity.

A general desire in the field of endoscopy is to electrically insulate the insertion tube, and thus the tip part, from the outside, so as to prevent or at least reduce the risk of an insulation breakdown and a resulting excessive leakage current. In particular it is desired that electrically conductive components, such as metal components, are positioned at a distance to the outer circumference of the insertion tube.

A general desire in the field of endoscopy is provide a tip part which is sealed, so as to reduce or prevent liquid ingress into the tip part, and specifically into any electrical components of the tip part.

A general desire in the field of endoscopy is to miniaturize the insertion tube of the endoscope, and thus the tip part, as this opens up new fields of application, for instance endoscopes for Ear, Nose, and Throat (ENT) endoscopy, such as rhinoscopy or rhinolaryngoscopy, which requires an insertion tube with a smaller footprint than for instance bronchoscopy.

Patent application US 2008/242935 A1 discloses an endoscope with a top cover. A lens barrel is fitted into and cemented to the top cover. Alternatively, a peripheral barrel portion is cemented and fixed to both surfaces of a soft tube covering a side surface of a distal end and a lens barrel.

Patent application US 2014/0210976 A1 discloses a camera assembly for an endoscope with a T-shaped flexible circuit board to better fit into a pipe of the endoscope.

Patent application WO 2010/066790 A1 discloses an endoscope having a camera housing made of a polymer based material of the kind which cures faster when exposed to ultraviolet light. A camera device is embedded in the material of the camera housing and a light source is embedded in the material of the camera housing.

However, the process of moulding a camera housing by curing using ultraviolet light is relatively slow and therefore expensive. This is especially the case for a single use endoscope. A further drawback is that the process requires relatively high operator skill as camera device has to be positioned and held accurately and the curing process has to be controlled carefully in order to obtain uniform wall thickness. In order to compensate for the variation in the moulding process the wall thickness is generally oversized so as to ensure for instance liquid tightness. Another drawback is that an ultraviolet-curing polymer material tend to change the experienced colour of a light source emitting light through the material. This is undesired as the hue of the illumination, and thus the captured image, will be changed typically towards blue.

Another endoscope with a camera assembly is manufactured according to the above-described principles in US 2014/0210976 A1 and is assembled in a tip part according to the principles of WO 2010/066790 A1. A bending section of this endoscope extends to enclose the sides of the camera assembly and the camera assembled is embedded in ultraviolet hardened adhesive, which seals the front of the camera assembly.

In a tip part for single-use endoscopes, the preferred way of assembling the parts of the tip part is by adhesion as this is low-cost, improves liquid tightness, and flexible as adhesion can typically be implemented with a wide range of part geometries. However, the bending section is generally made of an elastic polyolefin material to allow sufficient elasticity for a high quality manoeuvring of the endoscope, while still keeping material costs low to allow the manufacture of a single-use endoscope. A drawback of this group of materials is that they are usually difficult to adhere to, and thus presents a challenge when assembling the parts of the endoscope. Examples of such a material used for the bending section is a polyolefin material with low surface energy, such as plastics or elastomer, for instance Polypropylene (PP), Polyethylene (PE), or Polyoxymethylene (POM).

SUMMARY

On this background, it may be seen as an object of the present disclosure to provide an improved tip part for an endoscope, which at least mitigates some of the above-mentioned drawbacks.

One or more of these objects may be met by the disclosed embodiments as described in the following.

An articulated tip part for an endoscope, an endoscope including the articulated tip part, and a method of assembling the articulated tip part and the endoscope are provided.

A first aspect of the disclosure relates to a method for manufacture of a tip part for an endoscope, said method comprising:

providing a camera assembly with an image sensor, a lens barrel positioned at a distal end of the camera assembly, and a circuit board positioned at a proximal end of the camera assembly;

providing an exterior housing comprising a circumferential wall enclosing a spacing, the exterior housing further comprising a distal end wall, the distal end wall being integral with the circumferential wall and having an opening;

inserting the lens barrel of the camera assembly in the spacing of the exterior housing so that a distal end of the lens barrel extends into the opening, and so that an axially extending adhesive spacing is provided between the opening and the lens barrel along a circumference of the lens barrel, a radial extent of the adhesive spacing gradually being reduced in a direction towards the spacing of the exterior housing;

injecting an adhesive into the adhesive spacing;

allowing or causing the adhesive to harden so as to adhere the lens barrel to the distal end wall of the exterior housing.

This may provide the advantage, among others, that the risk of adhesive flowing onto the light emitting surface of the at least one light source may be reduced, mitigating the above-mentioned drawbacks of using adhesive near a light source.

Another advantage, among others, of the method may be that the material in front of camera assembly, specifically in front of a light source of the camera assembly, may be chosen to provide desired properties, such as transparency, without limitations of the material properties of UV hardened adhesives, so that an undesired color change of illumination provided by the light source may be avoided.

A limiting component on the reduction of circumference generally is the image sensor of the camera assembly. In some embodiments, there would usually be a layer of hardened adhesive, a circumferential wall of the distal end segment, and a sleeve surrounding the camera assembly. By manufacturing a tip part by the method disclosed herein, the outer circumference of the tip part may be made smaller by doing away with the layer of hardened adhesive and the circumferential wall of the distal end segment surrounding the camera assembly and instead having the exterior housing, which may be manufactured separately with a thinner wall thickness and with tighter tolerances, potentially by injection moulding, positioned to enclose the camera assembly.

By manufacturing a tip part by the method according to the embodiments of the disclosure, a separate mould and the associated disadvantages may be dispensed with. This method may reduce the required operator skill and thus, in some embodiments, the method may potentially be automated.

The radial extent of the adhesive spacing (the adhesive spacing may also be referred to as the "gap") may be measured in a radial direction of a line. The line may be a rotational symmetry line of the adhesive spacing, a centre line of the exterior housing, or the proximal-distal axis.

The step of allowing or causing the adhesive to harden may be performed so as to adhere the lens barrel to the opening of the distal end wall of the exterior housing.

Additionally, or alternatively the adhesive spacing may be provided so that when injecting an adhesive into the adhesive spacing the adhesive is drawn into the adhesive spacing by capillary action.

This may provide the advantage that the adhesive may be urged to fill the adhesive spacing if enough adhesive is provided.

The adhesive may be drawn fully or completely into the adhesive spacing by capillary action.

Additionally, or alternatively, the exterior housing and the camera assembly may be held in a substantially upright orientation, so that the distal end wall of the exterior housing is substantially facing upwards, while injecting the adhesive into the adhesive spacing.

This may provide the advantage that the risk of adhesive flowing onto the light emitting surface is reduced.

Additionally, or alternatively, the adhesive spacing may direct injected adhesive away from the light emitting surface of the at least one light source.

This may provide the advantage that the risk of adhesive flowing onto the light emitting surface is reduced.

The proximal end of the adhesive spacing may be positioned, so that a line between an edge of the light emitting surface closest to the proximal end of the adhesive spacing forms an angle in relation to the proximal-distal axis. The angle may be more than 45°, 50°, 55°, 60°, 65°, 70°, 75°, 80°, or 85°. The line may extend, potentially uninterrupted, in the spacing of the exterior housing, which spacing may also be referred to as the "internal volume" of the exterior housing.

The proximal end of the adhesive spacing may terminate in the spacing of the exterior housing.

A second aspect of the disclosure relates to a tip part for an endoscope, comprising:

a camera assembly with an image sensor, a lens barrel positioned at a distal end of the camera assembly, and a circuit board positioned at a proximal end of the camera assembly;

an exterior housing comprising a circumferential wall enclosing a spacing, the exterior housing further comprising a distal end wall, the distal end wall being integral with the circumferential wall and having an opening; and the lens barrel of the camera assembly being positioned in the spacing of the exterior housing so that a distal end of the lens barrel extends into the opening, an axially extending adhesive spacing being provided between the opening and the lens barrel along a circumference of the lens barrel, wherein a radial extent of the adhesive spacing gradually being reduced in a direction towards the spacing of the exterior housing, a hardened adhesive being positioned in the adhesive spacing and adhering the lens barrel to the distal end wall of the exterior housing.

Additionally, or alternatively, the adhesive spacing may have a distal end and a proximal end. The proximal end may be positioned in proximity to the spacing of the exterior housing, and the distal end may be positioned in proximity to the exterior.

Additionally, or alternatively, the hardened adhesive may be optically opaque, such as having a black colour. This may provide the advantage that light may be further prevented from ingressing into the side of the lens barrel to reduce the image quality of the image sensor.

Additionally, or alternatively, the adhesive spacing may be V-shaped. The adhesive spacing may narrow, potentially linearly, from the distal end towards to proximal end.

This may provide the advantage that the capillary action effect is increased as the adhesive is drawn into the adhesive spacing and may ensure that the adhesive spacing is fully filled.

The adhesive spacing may be defined by a lens barrel surface and an exterior housing surface. The lens barrel surface and the exterior housing surface both extends radially and substantially axially in relation to the proximal-distal axis.

Additionally, or alternatively, the camera assembly may comprise at least one light source with a light emitting surface configured to emit light distally. The adhesive spacing may extend at least to a point substantially aligned with the light emitting surface of the at least one light source.

This may provide the advantage, that the risk of adhesive flowing onto the light emitting surface of the at least one light source may be reduced, mitigating the above-mentioned drawbacks of using adhesive near a light source.

The adhesive spacing may extend, so that the proximal end of the adhesive spacing is positioned at least as proximal as the light emitting surface of the at least one light source.

Additionally, or alternatively, the radial extent of the adhesive spacing may be at least 1.5 times, potentially at least 2 times, preferably at least 3 times greater at the distal end than at the proximal end.

It has been found that providing the adhesive spacing in this way may be particularly advantageous.

The axial extent of the adhesive spacing may be at least 5 times, 10 times, 15 times, 20 times, 25 times, 30 times, 35 times, or 40 times greater than the radial extent of the adhesive spacing at the proximal end thereof.

It has been found that providing the adhesive spacing in this way may be particularly advantageous.

Additionally, or alternatively, the lens barrel may extend further distally than the distal end wall of the exterior housing.

This may reduce the risk of adhesive unintentionally flowing onto the lens barrel, potentially onto a lens of the lens barrel.

Additionally, or alternatively, the adhesive spacing may extend further proximally in relation to an interior surface of the exterior housing configured for propagating light received from the associated light source there through to the exterior. This may provide advantage that when adhesive is injected into the adhesive spacing reducing the risk of adhesive flowing onto the interior surface and potentially ending up on the light emitting surface of the associated light source.

"Propagating" light may throughout this application alternatively be denoted "transferring" light.

It has been found that providing the adhesive spacing in this way may be particularly advantageous.

Additionally, or alternatively, the hardened adhesive positioned in the adhesive spacing may seal the adhesive spacing, so as to provide a fluidly sealed distal tip end of the tip part.

This may provide the advantage that the liquid tightness of the tip part is further improved, so as to protect electronic components of the tip part.

Additionally, or alternatively, a proximal end of the exterior housing may be secured and sealed to a distal end segment of a bending section.

Additionally, or alternatively, the tip part according to the second aspect of the disclosure may form part of an endoscope, the tip part may be positioned at a distal end of the endoscope.

The term "endoscope" may be defined as a device suitable for examination of natural and/or artificial body openings, e.g. for exploration of a lung cavity. Additionally, or alternatively, the term "endoscope" may be defined as a medical device.

The endoscope may comprise the control element. The control element may be configured to allow an operator to control the steerable tip part of the insertion tube by the at least one steering wire. The control element may allow bending the steerable tip part in at least one direction, potentially in two directions, the two directions potentially being opposite. The control element may be accommodated in the operating handle. The control element may include a lever allowing an operator to control the control element. The lever may extend outwardly from the control element, potentially through the operating handle. The control element may be in the form of a roller or a roller disc.

The endoscope may comprise an operating handle. The operating handle may be suitable for allowing an operator to grip and to operate the endoscope, potentially with one hand. The operating handle may comprise a handle housing arranged at a proximal end of the insertion tube. The handle housing may accommodate the control element.

The insertion tube or a distal end thereof may be suitable for insertion into a body cavity, potentially a lung, through a body opening, potentially a mouth. The body may be a natural and/or artificial body, potentially a human body. The insertion tube may extend from the operating handle towards a distal end of the endoscope.

Additionally, or alternatively, the endoscope may form part of a system for visually inspecting inaccessible places such as human body cavities, the system further comprising a monitor. The endoscope may be connectable to the monitor, and the monitor may allow an operator to view an image captured by the camera assembly of the endoscope.

The tip part according to the second aspect of the disclosure may be combined with the tip part according to the third aspect of the disclosure. This may provide the advantage that the liquid tightness of the tip part may be further improved as the electronic components of the camera module and of the printed circuit board may be sealed both from a distal end thereof and a proximal end thereof.

A third aspect of the disclosure relates to a method for manufacture of a tip part for an endoscope, said method comprising the steps of:
  (a) providing a camera assembly with an image sensor and a circuit board, the camera assembly having a distal end and a proximal end, the circuit board being positioned at the proximal end;
  (b) providing a distal end segment having a circumferential wall enclosing a spacing, said distal end segment having a distal end;
  (c) providing an exterior housing comprising a circumferential wall enclosing a spacing and a proximal end;
  (d) inserting the distal end of the camera assembly in the spacing of the exterior housing;

(e) positioning the proximal end of the exterior housing adjacent to the distal end of the distal end segment, so that the distal end segment and the exterior housing enclose the camera assembly;

(f) injecting an adhesive into the spacing of the distal end segment so that at least parts of the circuit board are embedded in the adhesive;

(g) allowing or causing the adhesive to harden; and (h) whereby the distal end segment, camera assembly and exterior housing form an assembled tip part of an endoscope attached to each other by means of the adhesive.

Additionally, or alternatively, the distal end segment may form part of, potentially an integral part of, a bending section of the tip part. The bending section may allow the operator to bend this section, potentially by manipulation of a control element of an endoscope, thus the tip part is an articulated tip part.

In this specification, the proximal-distal axis may be defined as an axis extending along the parts of the insertion tube of the endoscope. Adhering to the definition of the terms distal and proximal, i.e. proximal being the end closest to the operator and distal being the end remote from the operator. The proximal-distal axis is not necessarily straight, for instance if the insertion tube is bent then the proximal-distal axis follows the curvature of the insertion tube. The proximal-distal axis may for instance be a centre line of the insertion tube.

By manufacturing a tip part by the method according to embodiments of the disclosure, a separate mould and the associated disadvantages may be dispensed with. This method may reduce the required operator skill and thus the method may potentially be automated.

Another advantage of the method may be that the material in front of the camera assembly, specifically in front of a light source of the camera assembly, may be chosen to provide desired properties, such as transparency, without limitations of the material properties of UV hardened adhesives, so that an undesired color change of illumination provided by the light source may be avoided.

It has been recognized by the inventors that the limiting component on the reduction of circumference generally is the image sensor of the camera assembly. In the prior art there would usually be a layer of hardened adhesive, a circumferential wall of the distal end segment, and a sleeve surrounding the camera assembly. By manufacturing a tip part by this method, the outer circumference of the tip part may be made smaller by doing away with the layer of hardened adhesive and the circumferential wall of the distal end segment surrounding the camera assembly and instead having the exterior housing, which may be manufactured separately with a thinner wall thickness and with tighter tolerances, potentially by injection moulding, positioned to enclose the camera assembly.

This method may provide the advantage that liquid tightness is ensured by having an exterior housing which may ensure that a barrier of solid material is provided between the circuit board and the exterior of the tip part, thus contributing to the liquid tightness of the tip part. Additionally, the advantage of providing liquid tightness to the circuit board by adhesive may still be preserved serving as a second layer of sealing for the electronic components of the circuit board, and thus improving liquid tightness of the tip part.

The method may provide the advantage, that the challenge of adhering to the bending section may be mitigated as the adhesive may secure both circuit board, the exterior housing and the distal end segment of the bending section to each other, thus increasing the adhered surface area.

The steps of the method according to the first aspect of the disclosure may be performed without placing the exterior housing and/or the bending section in a mould.

The steps of the method may be performed in any order, not necessarily in sequence. A sequence of method steps may be (a), (c), (d), (b), (e), (f), (g). In some embodiments, the steps of the method are performed in alphabetical order of the step designation. Steps (a), (b), and (c) may be performed simultaneously.

In step (c), the exterior housing may be provided by manufacturing the exterior housing by an injection moulding process.

The step (d) may divide the spacing of the exterior housing into a proximal spacing and a distal spacing. A circumference of the camera assembly extending around the image sensor may provide a border, potentially a sealed border between the proximal and the distal spacing.

The step (d) may further comprise sealing a gap between a circumference of the camera assembly extending radially around the image sensor of the camera assembly and an interior surface of the exterior housing.

In step (d), the camera assembly may be inserted into the distal spacing of the exterior housing so that a light emitting surface of a light source abuts the exterior housing.

This may provide the advantage that the light emitting surface can emits light along an optical axis substantially parallel to the proximal-distal axis as it may otherwise be difficult to ensure this due to the elasticity of the printed circuit board onto which the light source(s) is/are mounted.

The adhesive may be curable by exposure to ultraviolet (UV) light, and/or the step (g) may be performed by exposing the adhesive to ultraviolet light.

The camera assembly may include a lens barrel having at least one lens, potentially a plurality of lenses.

The distal end segment may form part of a bending section. The bending section may comprise a number of hingedly interconnected segments including the distal end segment, a proximal end segment, and a plurality of intermediate segments positioned between the proximal end segment and the distal end segment. At least one hinge member interconnects adjacent segments with each other. The bending section may be a section allowing the tip part to bend relative to the insertion tube, potentially so as to allow an operator to manipulate the tip part while inserted into a body cavity of a patient.

The exterior housing, the distal end segment, and the camera assembly may be provided separately and/or as separate components. The steps (a), (b), and (c) may be performed separately and/or independently of each other.

Additionally, or alternatively, step (e) may comprise positioning the proximal end of the exterior housing in abutment with the distal end of the distal end segment of the bending section, so that the distal end segment of the bending section and the exterior housing enclose the camera assembly.

This may further improve the liquid tightness of the tip part as exterior surfaces made of hardened adhesive are reduced.

Additionally, or alternatively, step (e) may comprise overlapping the proximal end of the exterior housing and the distal end of the distal end segment of the bending section.

This may provide the advantage that the connection between the proximal end of the exterior housing and the distal end of the distal end segment of the bending section is further improved as the surface area of adhesion is increased between the exterior housing and the distal end segment.

The proximal end of the exterior housing may overlap the distal end of the distal end segment of the bending section, potentially so that the proximal end of the exterior housing is positioned exteriorly relative to the distal end of the distal end segment of the bending section.

Step (f) may include injecting the adhesive into the spacing of the distal end segment of the bending section so that a gap in the overlap of the proximal end of the exterior housing and the distal end of the distal end segment of the bending section is filled with the adhesive, potentially so that the adhesive seals the gap in the overlap and/or attaches the proximal end of the exterior housing and the distal end of the distal end segment of the bending section to each other by the overlap.

Additionally, or alternatively, step (f) may comprise injecting the adhesive into the spacing of the distal end segment of the bending section through an adhesive injection hole in the exterior housing and/or the distal end segment of the bending section.

This may provide a particularly simple way of performing the method as the adhesive injection hole for the specific purpose of injecting adhesive is provided and may provide a visual indication as to where to inject adhesive.

Additionally, or alternatively, the step of injecting the adhesive may be performed by means of an injection tube inserted into the adhesive injection hole. The viscosity of the adhesive may be selected so that the adhesive does not substantially flow back out the adhesive injection hole from the spacing of the distal end segment once the injection tube is removed from the adhesive injection hole.

Additionally, or alternatively, the method according to the first aspect may comprise a step, potentially performed simultaneously with the step (f), of:
  (i) providing a measurement of the volume of the injected adhesive into the spacing of the distal end segment of the bending section.

This may provide a way of allowing automation of the assembly of the tip part. This may also provide a way of controlling the volume of injected adhesive, so as to ensure that sufficient adhesive is injected to provide adequate liquid tightness while ensuring that not too much adhesive is injected as this may reduce the flexibility of the bending section.

The step (h) may be achieved by one or more of the following ways:
  a vision measurement device visually inspecting the level of the injected adhesive in the spacing of the distal end segment of the bending section, potentially through a translucent or transparent material of the distal end segment of the bending section and/or the proximal end of the exterior housing; and/or
  a pressure measurement device measuring the pressure in the spacing of the distal end segment of the bending section; and/or
  an injection volume measurement device measuring the amount of adhesive being injected into the spacing of the distal end segment of the bending section; and/or
  a motion detection device detecting a fluid level of the adhesive in the spacing of the distal end segment of the bending section; and/or
  a timing device measuring a time elapsed during the injection of the adhesive into the spacing of the distal end segment of the bending section and calculating the volume injected by a predetermined flow rate of the adhesive.

Step (h) may be performed continuously and may allow the provision of a feed-back control loop for controlling the injected adhesive.

The step (h) may comprise stopping the injection of adhesive into the spacing of the distal end segment of the bending section once the measurement of the volume of the injected adhesive equals or exceeds a predetermined volume of adhesive.

Additionally, or alternatively, step (f) may include injecting the adhesive into the spacing of the distal end segment of the bending section so that the adhesive overlaps a distal end of a tube surrounding an electronic cable connected to the circuit board.

This may provide the advantage that liquid tightness is further improved as the proximal end of the circuit board and the electronic cable connecting the circuit board, for instance to a monitor, is sealed off by the adhesive.

Additionally, or alternatively, the step (d) may divide the spacing of the exterior housing into a distal cavity in the distal end of the exterior housing, in which a light emitting surface is positioned, and a proximal cavity, the method according to the first aspect may further comprise a step of:
  (i) sealing the distal cavity from the proximal cavity.

This may provide the advantage that the light emitting surface is sealed from the injected adhesive, and thus consistent light emitting properties of the light emitting surface may be ensured as the light emitted only has to propagate through the exterior housing, which may be more accurately controlled than adhesive.

The light emitting surface may form part of a light source, such as a LED. The step (i) may be performed prior to the step (f). The step (i) may comprise sealing the interior cavity from a proximal cavity of the exterior housing, the circuit board may be positioned in the proximal cavity.

The step (i) may be performed by:
  adhering a circumference of the camera assembly to an interior surface of the circumferential wall of the exterior housing; and/or
  providing a gasket between a circumference of the camera assembly and an interior surface of the circumferential wall of the exterior housing; and/or
  welding a circumference of the camera assembly to an interior surface of the circumferential wall of the exterior housing.

Additionally or alternatively, the camera assembly may include a lens barrel positioned at a distal end of the camera assembly, and the exterior housing may further comprise a distal end wall, the distal end wall may be integral with the circumferential wall and may have an opening, wherein the method according to the first aspect of the disclosure may further comprise a step of:
  inserting the lens barrel of the camera assembly in the spacing of the exterior housing so that a distal end of the lens barrel extends into the opening, and so that an axially extending adhesive spacing is provided between the opening and the lens barrel along a circumference of the lens barrel, a radial extent of the adhesive spacing gradually being reduced in a direction towards the spacing of the exterior housing,
  injecting an adhesive into the adhesive spacing, and
  allowing or causing the adhesive to harden so as to adhere the lens barrel to the distal end wall of the exterior housing.

Additionally, or alternatively, the method according to the first aspect may comprise a step of:
  (j) positioning a sleeve or external sheath around the exterior housing and the distal end segment of the bending section.

This may provide an additional layer of sealing for the connection between the exterior housing and the distal end segment. The sleeve or external sheath may also provide a smooth outer surface for the bending section in order to improve the comfort of a patient undergoing endoscopy.

Step (j) may further comprise sealing the sleeve or external sheath to the exterior housing and the distal end segment of the bending section.

A fourth aspect of the disclosure relates to a tip part for an endoscope, comprising:

a camera assembly with an image sensor and a circuit board, the camera assembly having a distal end and a proximal end, the circuit board being positioned at the proximal end;

a bending section with a distal end segment having a circumferential wall enclosing a spacing, said distal end segment having a distal end;

an exterior housing comprising a circumferential wall enclosing a spacing and a proximal end being adjacent the distal end of the distal end segment of the bending section;

wherein the distal end of the camera assembly is positioned in the spacing of the exterior housing;

wherein the proximal end of the camera assembly is positioned in the spacing of the distal end segment of the bending section, the distal end segment of the bending section and the exterior housing enclosing the camera assembly; and wherein a hardened adhesive provided separately from the exterior housing substantially fills out the spacing of the distal end segment of the bending section so that at least parts of the circuit board are embedded in the adhesive, the hardened adhesive attaching or fixing the bending section, camera assembly and exterior housing to each other.

The camera assembly may be a sub-assembly of the tip part.

The camera assembly may comprise a lens barrel enclosing at least one lens, potentially a plurality of lenses. The lens barrel may alternatively be formed integrally in one piece with the exterior housing.

The at least one lens, potentially the plurality of lenses, may be of one or more types chosen from the group consisting of: concave, convex, plano-concave, plano-convex, bi-convex, bi-concave.

The camera assembly may comprise a mounting frame. The mounting frame may support and/or secure one or more of the group consisting of: the printed circuit board, the light source(s), the lens barrel, and the image sensor.

The camera assembly may comprise at least one, potentially two, light source(s) with a light emitting surface. The light emitting surface(s) may not be embedded in the hardened adhesive. The light emitting surface(s) may emit light in a direction substantially parallel to the proximal-distal direction. The light emitting surface(s) may be positioned in abutment with the exterior housing.

The hardened adhesive may also partly be positioned in the spacing, potentially the proximal spacing, of the exterior housing. The hardened adhesive may be in contact with a surface, specifically an interior surface, of the exterior housing and/or a surface, specifically an interior surface, of the distal end segment. The exterior housing and the hardened adhesive may be of different materials. Potentially, the hardened adhesive does not surround all parts of the camera assembly, specifically the hardened adhesive does not surround the distal end of the camera assembly. Potentially, the hardened adhesive is not in contact with the light emitting surface(s) of the camera assembly.

That the hardened adhesive is being provided separately from the exterior housing does not necessarily include that the hardened adhesive and the exterior housing are not in contact with each other or positioned close to each other.

The proximal end of the exterior housing and the distal end of the distal end segment of the bending section may be positioned to be overlapping. The proximal end of the exterior housing may overlap the distal end of the distal end segment of the bending section, potentially so that the proximal end of the exterior housing is positioned exteriorly relative to the distal end of the distal end segment of the bending section. The hardened adhesive may seal a gap between the proximal end of the exterior housing and the distal end of the distal end segment of the bending section.

This may provide the advantage that the connection between the proximal end of the exterior housing and the distal end of the distal end segment of the bending section is further improved as the surface area of adhesion is increased between the exterior housing and the distal end segment.

The tip part may comprise a sleeve or external sheath enclosing the connection between the exterior housing and the distal end segment of the bending section. The sleeve or external sheath may at least partially seal the connection between the exterior housing and the distal end segment.

Additionally, or alternatively, the hardened adhesive may seal a gap between the proximal end of the exterior housing and the distal end of the distal end segment of the bending section.

Additionally, or alternatively, the hardened adhesive may be positioned in a connection between the proximal end of the exterior housing and the distal end of the distal end segment of the bending section, to seal the connection.

Additionally, or alternatively, the hardened adhesive may at least partially seal at least the proximal end of the circuit board.

Additionally, or alternatively, the exterior housing or the bending section may comprise an adhesive injection opening, potentially in the form of an adhesive injection hole.

This may provide a visual indication as to where to inject adhesive, so as to reduce the complexity of assembling the tip part. This may also ensure that adhesive is injected in the same location for every assembly increasing the reliability of the sealing and fixing properties of the adhesive.

The adhesive injection hole may be provided in the circumferential wall of the distal end segment and/or may be in communication with the spacing of the distal end segment.

The adhesive injection hole may be positioned at a proximal end of the exterior housing or at the distal end segment of the bending section or at a distal end of the distal end segment of the bending section. A first portion of the adhesive injection hole may be provided in the exterior housing and a second portion of the injection hole may be provided in the bending section, potentially so that when the exterior housing and the bending section are attached the first and second portion of the adhesive injection hole align to form the adhesive injection hole. An intermediate segment of the bending section adjacent to the distal end segment may comprise a cut-out aligned with the adhesive injection hole of the distal end segment of the bending section.

Another aspect of the disclosure relates to a tip part obtainable by the method according to the second or fourth aspect of the disclosure.

The method according to the first aspect of the disclosure may be combined with the method according to the third aspect of the disclosure. This may provide the advantage that the liquid tightness of the tip part may be further improved as the electronic components of the camera module and of the printed circuit board may be sealed both from a distal end thereof and a proximal end thereof.

A person skilled in the art will appreciate that any one or more of the above aspects of the disclosure and embodiments thereof may be combined with any one or more of the other aspects of the disclosure and embodiments thereof.

BRIEF DESCRIPTION OF DRAWINGS

The disclosure will now be described in greater detail based on non-limiting exemplary embodiments and with reference to the drawings, on which:

FIG. 4b shows a cross-sectional view of the tip part along the lines A-A of FIG. 4a;

FIG. 5b shows a cross-sectional view of the tip part along the lines B-B of FIG. 5a.

DETAILED DESCRIPTION

Figure 1A:
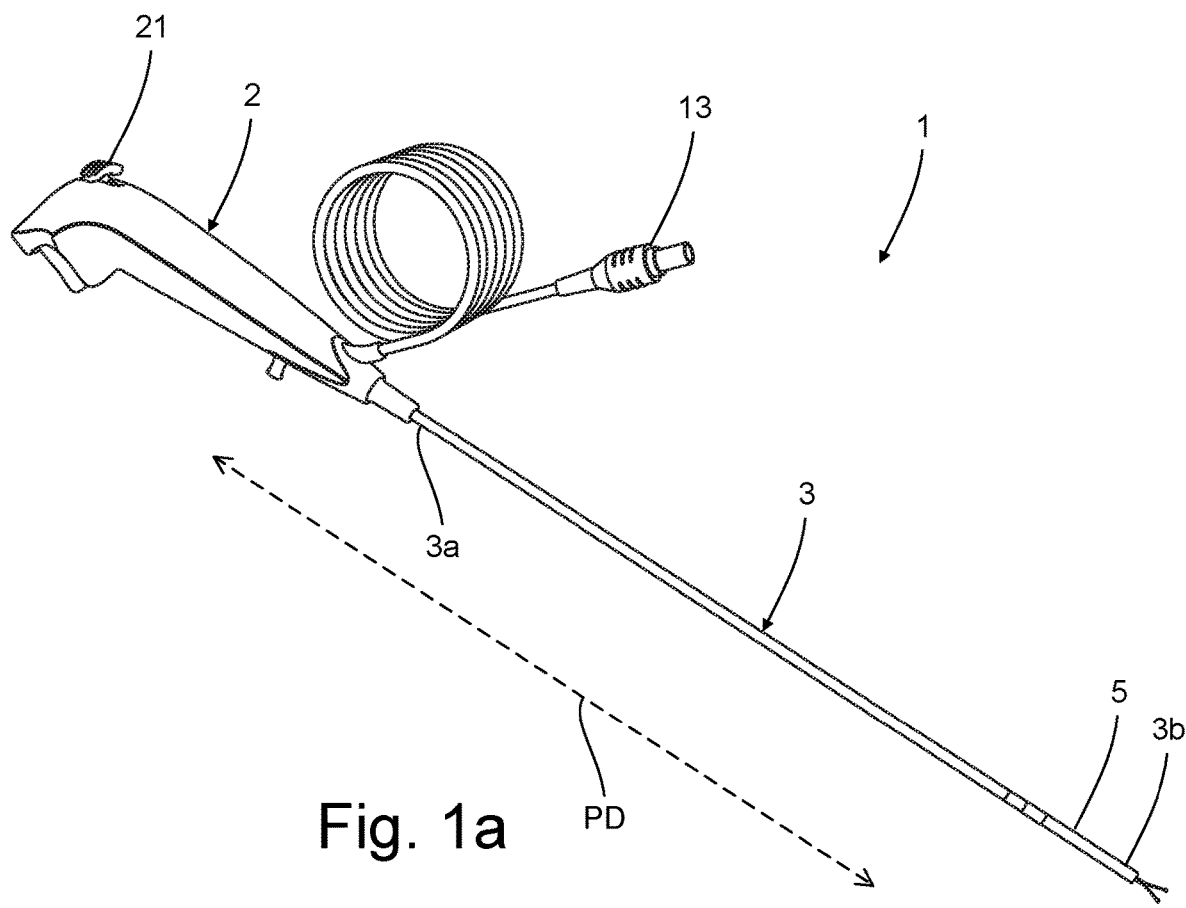
FIG. 1a shows a perspective view of an endoscope in which a tip part according to an embodiment of the present disclosure is implemented.

Referring first to FIG. 1a, an endoscope 1 is shown. The endoscope is disposable, and not intended to be cleaned and reused. The endoscope 1 comprises an elongated insertion tube 3. At the proximal end 3a of the insertion tube 3 an operating handle 2 is arranged. The operating handle 2 has a control lever 21 for manoeuvring an articulated tip part 5 at the distal end 3b of the insertion tube 3 by means of a steering wire 7 (visible in FIG. 5a). A camera assembly 6 is positioned in the tip part 5 and is configured to transmit an image signal through a monitor cable 12 of the endoscope 1 to a monitor 13.

Figure 1B:
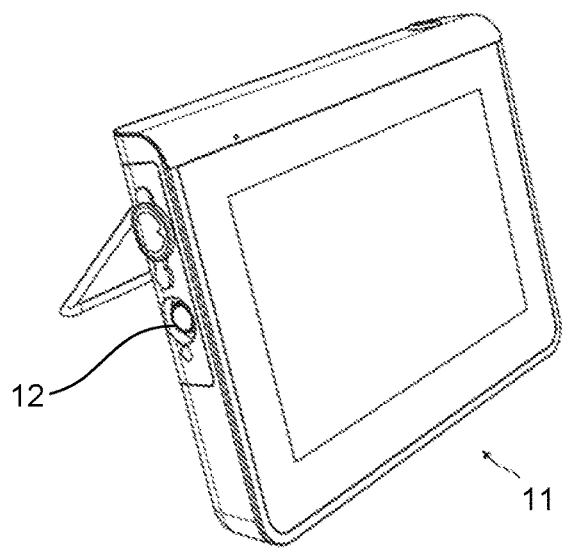
FIG. 1b shows a perspective view of a monitor to which the endoscope of FIG. 1a is connectable.

In FIG. 1b, a monitor 11 is shown. The monitor 11 may allow an operator to view an image captured by the camera assembly 6 of the endoscope 1. The monitor 11 comprises a cable socket 12 to which a monitor cable 13 of the endoscope 1 can be connected to establish a signal communication between the camera assembly 6 of the endoscope 1 and the monitor 11.

Figure 2A:
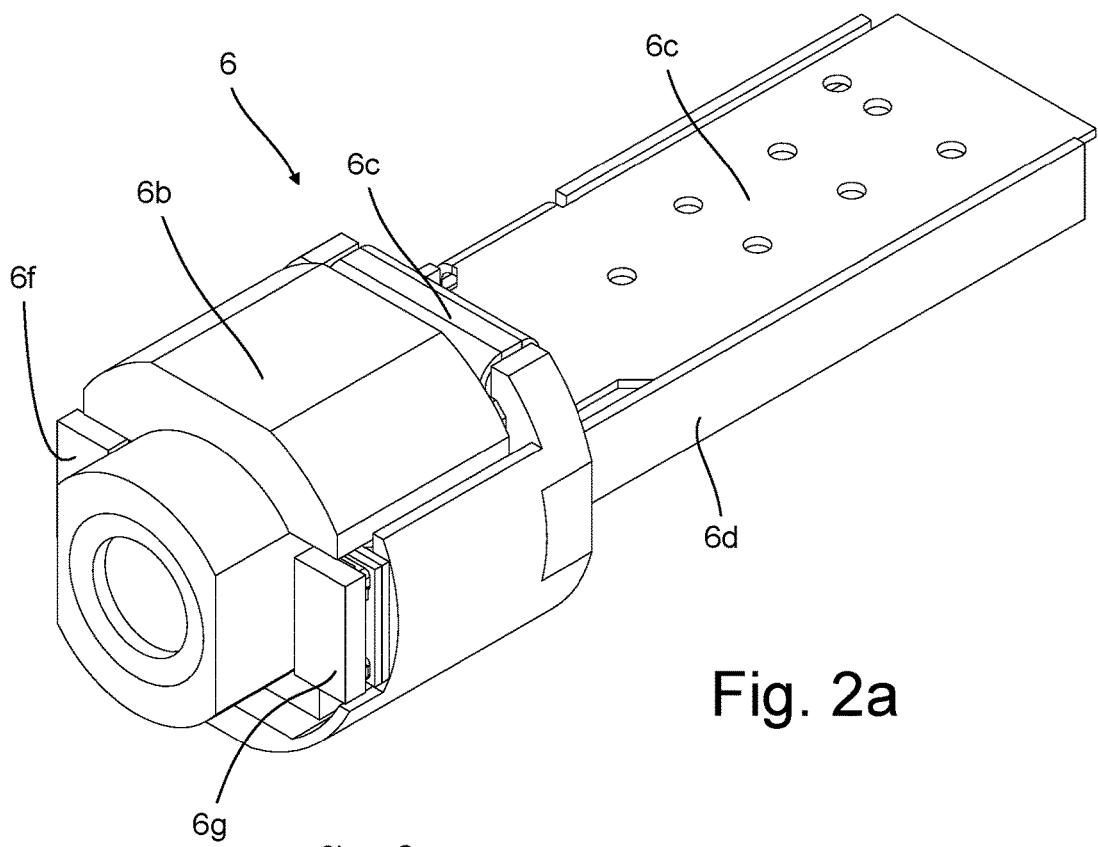
FIGS. 2a and 2b shows a perspective view of a camera assembly to be incorporated in a tip part according to the first aspect of the present disclosure.
Figure 2B:
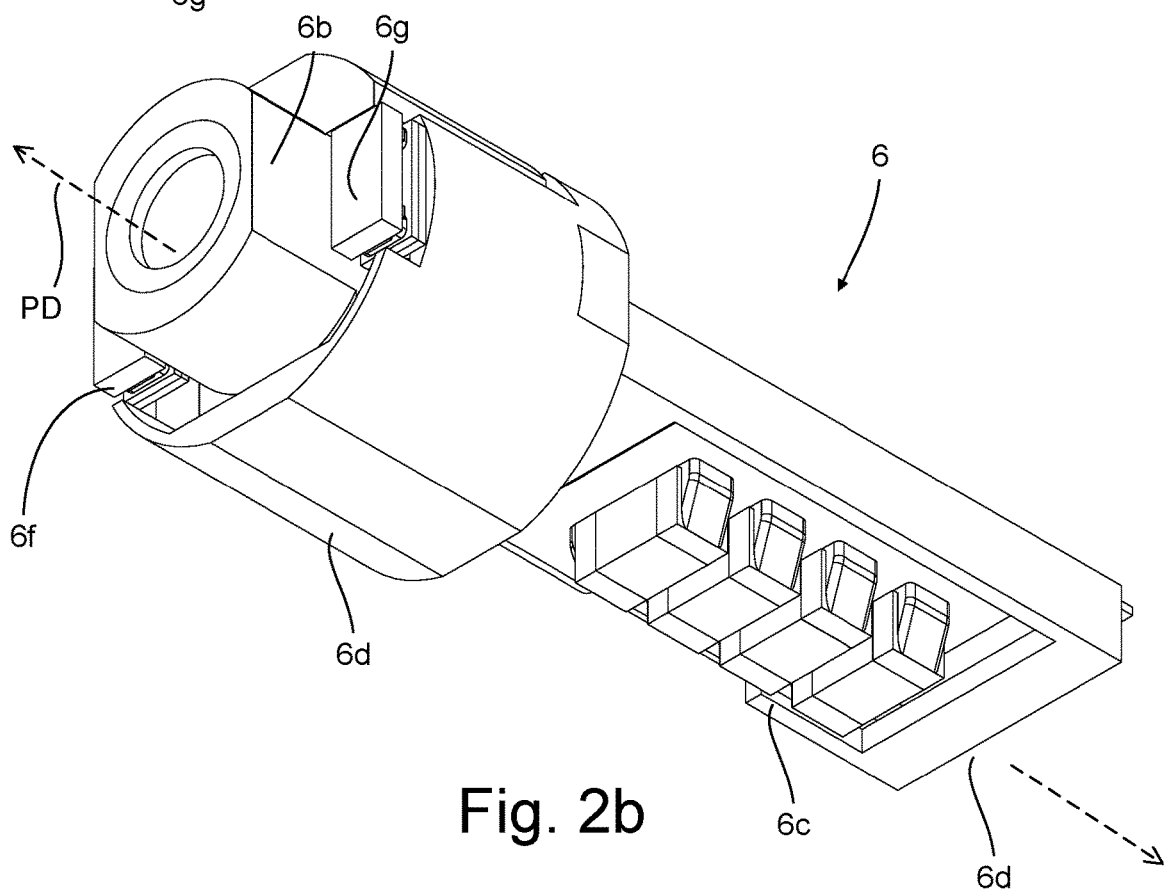

Turning first to FIGS. 2a and 2b, a camera assembly 6 is provided. The camera assembly 6 is to be incorporated in a tip part according to the present invention. The camera assembly comprises an image sensor 6a, a lens barrel 6b, a printed circuit board 6c, a mounting frame 6d, a first light source 6f, and a second light source 6g. The printed circuit board 6c is connected with at least one signal cable (not shown) and a power cable (not shown) prior to being assembled. The cables are accommodated in a cable tube 6e, which electrically and liquidly seals the cables. As better seen in FIGS. 4B and 5b, the image sensor 6a is connected with the printed circuit board 6c and is configured to capture an image from light received from the distal end 6i of the camera assembly. Generally, at least one lens is positioned in the lens barrel 6b in front of the image sensor 6a and is for providing adequate optical characteristics to the light received by the image sensor 6a. The at least one lens has however been omitted in these drawings. The two light sources 6f, 6g are in the form of light emitting diodes and are positioned on opposite sides of the lens barrel 6b and are configured to emit light through integrally provided lenses 17 on an interior surface 16 of the exterior housing 8 (see FIG. 6). The light emitted from the light sources 6f, 6g serve as illumination for the image sensor 6a. The mounting frame 6d provides support for the camera assembly and secures the flexible printed circuit board 6c, which is positioned at a proximal end 6h of the camera assembly 6. The mounting frame 6d allows the printed circuit board 6c to be folded around the mounting frame 6d. The mounting frame 6d also provides backing support to the light sources 6f, 6g so as to ensure that the light sources 6f, 6g emit light directly distally.

The camera assembly 6 may advantageously be assembled in accordance with the principles of commonly owned U.S. Pat. No. 9,622,649, which is incorporated herein by reference. Firstly, the substantially T-shaped printed circuit board 6c is provided. Then the image sensor 6a is positioned onto and connected to the printed circuit board 6c. The lens barrel 6b is then positioned on and secured to the image sensor 6a so that at least one lens of the lens barrel 6b is positioned in front of the image sensor 6a. Two arms of the printed circuit board 6c each comprising a light emitting diode 6f, 6g are then folded, so that the light emitting diodes 6f, 6g are positioned on opposite sides and near the front of the lens barrel 6b. The mounting frame 6d is then secured to the lens barrel 6b providing support for and securing the light sources 6f, 6g. A portion of the printed circuit board 6b comprising electrical components is then folded around and secured to the mounting frame 6d to obtain the camera module 6 as shown in FIGS. 2a-2b.

Figure 3A:
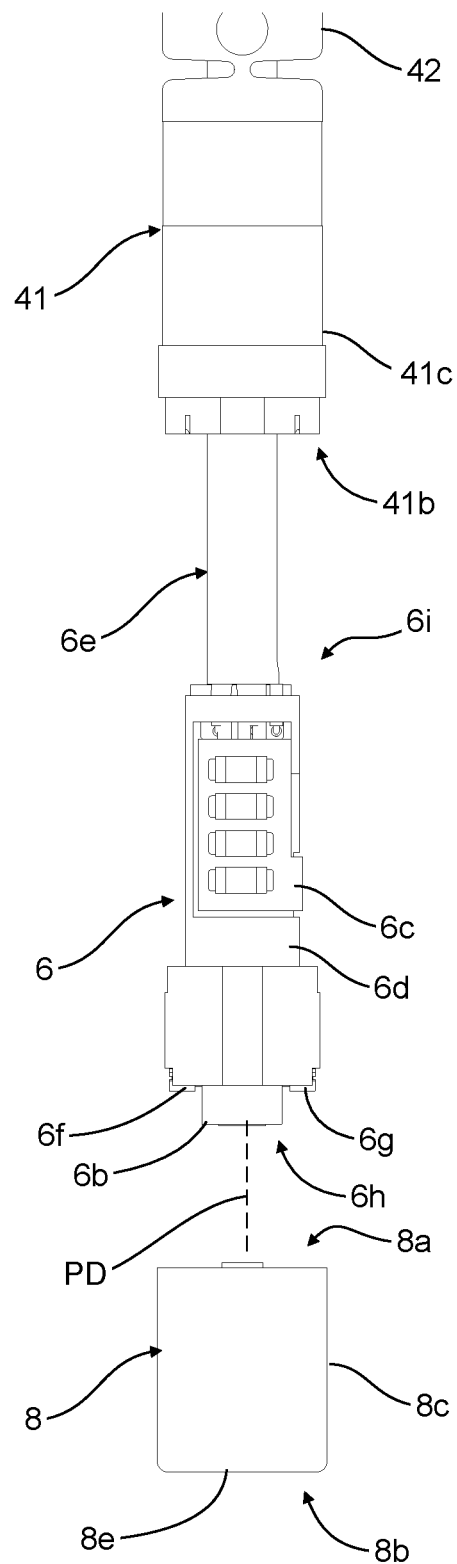
FIGS. 3a and 3b respectively shows a side view and a perspective view of a tip part prior to being assembled.
Figure 3B:
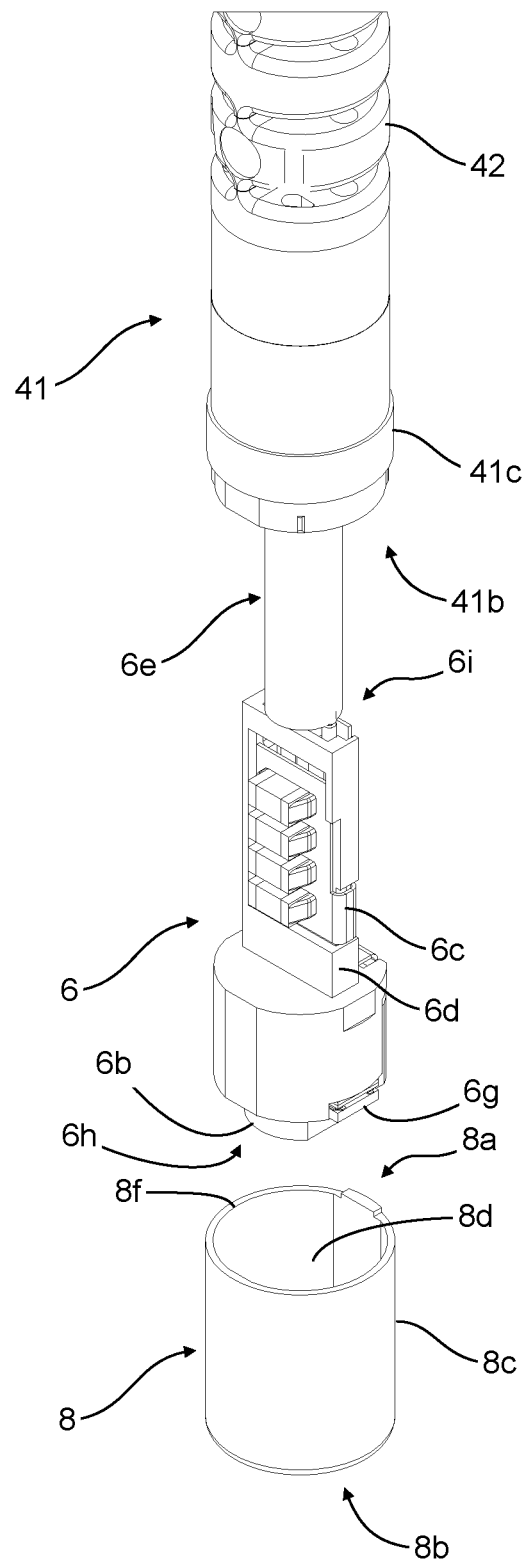

Turning to FIGS. 3a and 3b, an exterior housing 8 is provided. The exterior housing 8 is substantially cup-shaped and has a proximal end 8a and an opposite distal end 8b. The exterior housing comprises a circumferential side wall 8c enclosing an interior volume or spacing 8d, a distal end wall 8e with an opening 8f for the lens barrel 6b of the camera assembly 6. The opening 8f includes an inner surface 18. The camera assembly 6 of FIGS. 2a-2b is positioned at a distance above the exterior housing 8. The cables are positioned in a cable tube 6e and are connected to the printed circuit board 6c of the camera assembly 6. The cable tube 6e is positioned in a bending section 4 positioned at a distance above the camera assembly 6. The bending section comprises a number of hingedly connected segments including a distal end segment 41, a proximal segment 43, and a plurality of intermediate segments 42 positioned between the distal end segment 41 and the proximal segment 43. The distal end segment includes a circumferential side wall 41c enclosing a spacing 41d. The distal end segment 41 has an opening 41e for the camera assembly 6 positioned at a distal end 41b of the distal end segment 41.

Figure 4A:
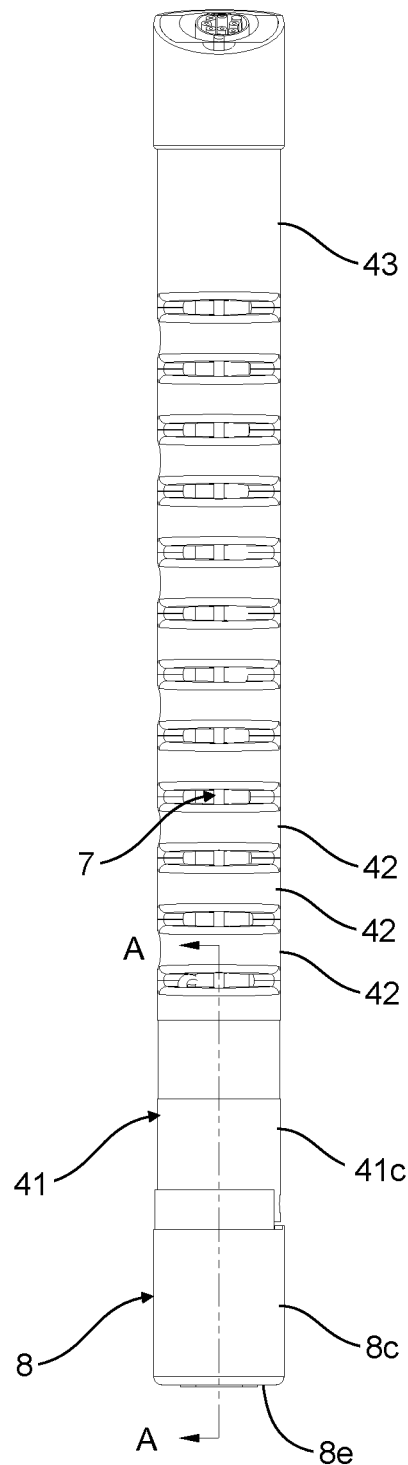
FIG. 4a shows a side view of the tip part of FIGS. 3a and 3b wherein the exterior housing and the distal end segment are positioned adjacently.
Figure 4B:
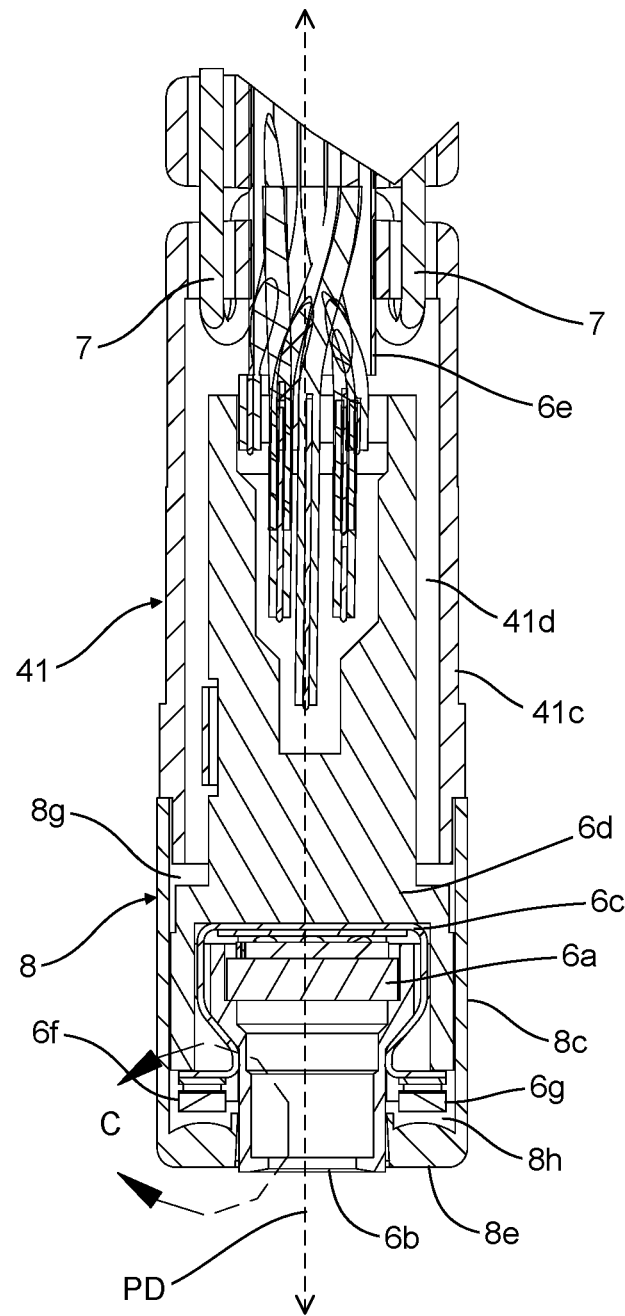

Turning to FIGS. 4a and 4b, the proximal end 8a of the exterior housing 8 is positioned in abutment with the distal end 41b of the distal end segment 41 of the bending section 4, so that the proximal end 8a of the exterior housing 8 overlaps the distal end 41b of the distal end segment 41, and so that the distal end segment 41 of the bending section 4 and the exterior housing 8 fully enclose the camera assembly 6.

Figure 5A:
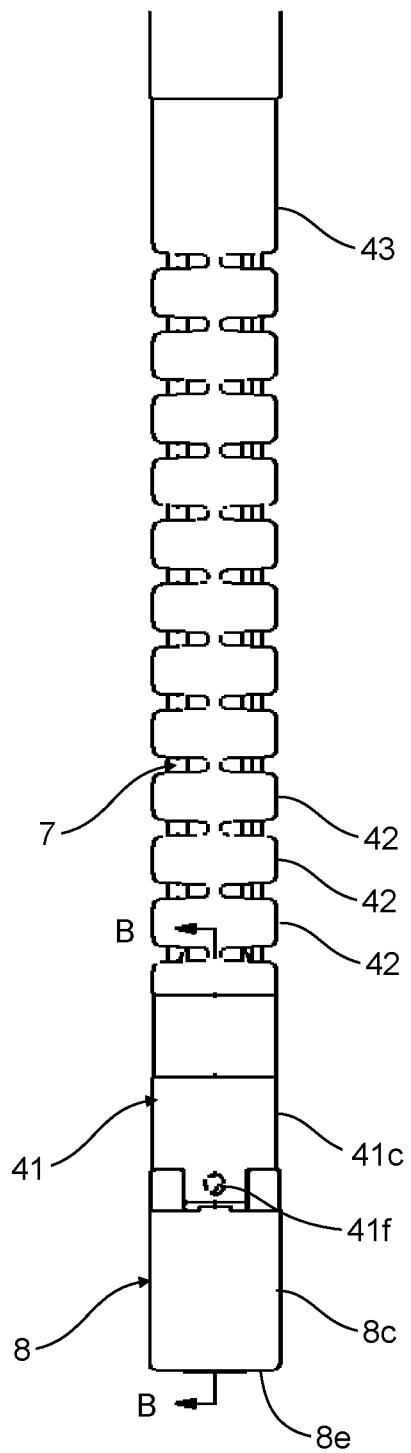
FIG. 5a shows a side view of the tip part of FIG. 4a during injection of adhesive.
Figure 5B:
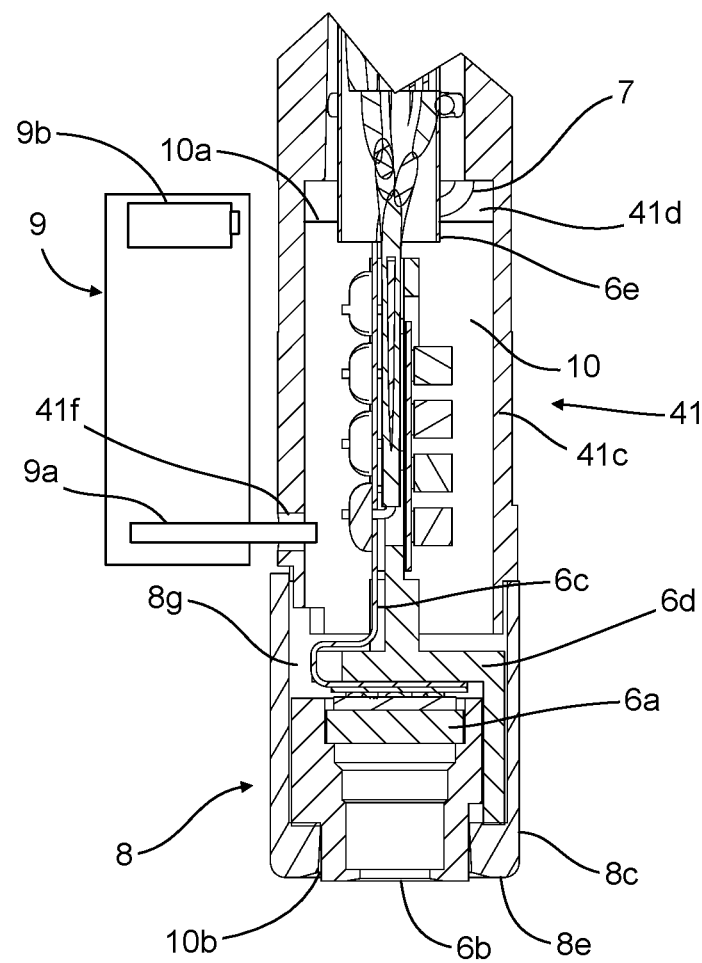

Turning to FIGS. 5a and 5b, in order to ensure liquid tightness of the tip part 5, the tip part 5 is held in an upright position, in which the distal end segment 41 is arranged directly above the exterior housing 8, so that the tip part 5 is arranged vertically. An adhesive 10 is then injected by an injection device 9 through an injection tube 9a into the spacing 41d of the distal end segment 41 of the bending section 4 through an adhesive injection hole 41f in the distal end segment 41. The adhesive injection hole 41f is provided in the circumferential side wall 41c of the distal end segment 41 and is in communication with the spacing 41d of the distal end segment 41. The adhesive 10 is injected until a level 10a of the adhesive 10 reaches above an opening of the cable tube 6e, so that the circuit board 6c is completely embedded in the adhesive 10. Then the injection tube 9a is removed from the adhesive injection hole 41f. The viscosity of the adhesive 10 may be selected so that the adhesive 10 does not substantially flow back out the adhesive injection hole 41f once the injection tube 9a is removed. When the injection tube 9a is removed, the adhesive 10 is caused to harden by exposure to ultraviolet light, so that the adhesive 10 fills and seals the spacing 41d and the adhesive injection hole 41f. Simultaneously with the injection of the adhesive, a control device 9b of the injection device 9 provides a measurement of the volume of the injected adhesive into the spacing of the distal end segment of the bending section and the adhesive level 10a by means of measuring the time elapsed while injecting through the injection tube 9a with a substantially constant flow rate, and detecting the adhesive level 10a in the spacing 41d of the distal end segment 41 by means of motion detection.

Figure 6:
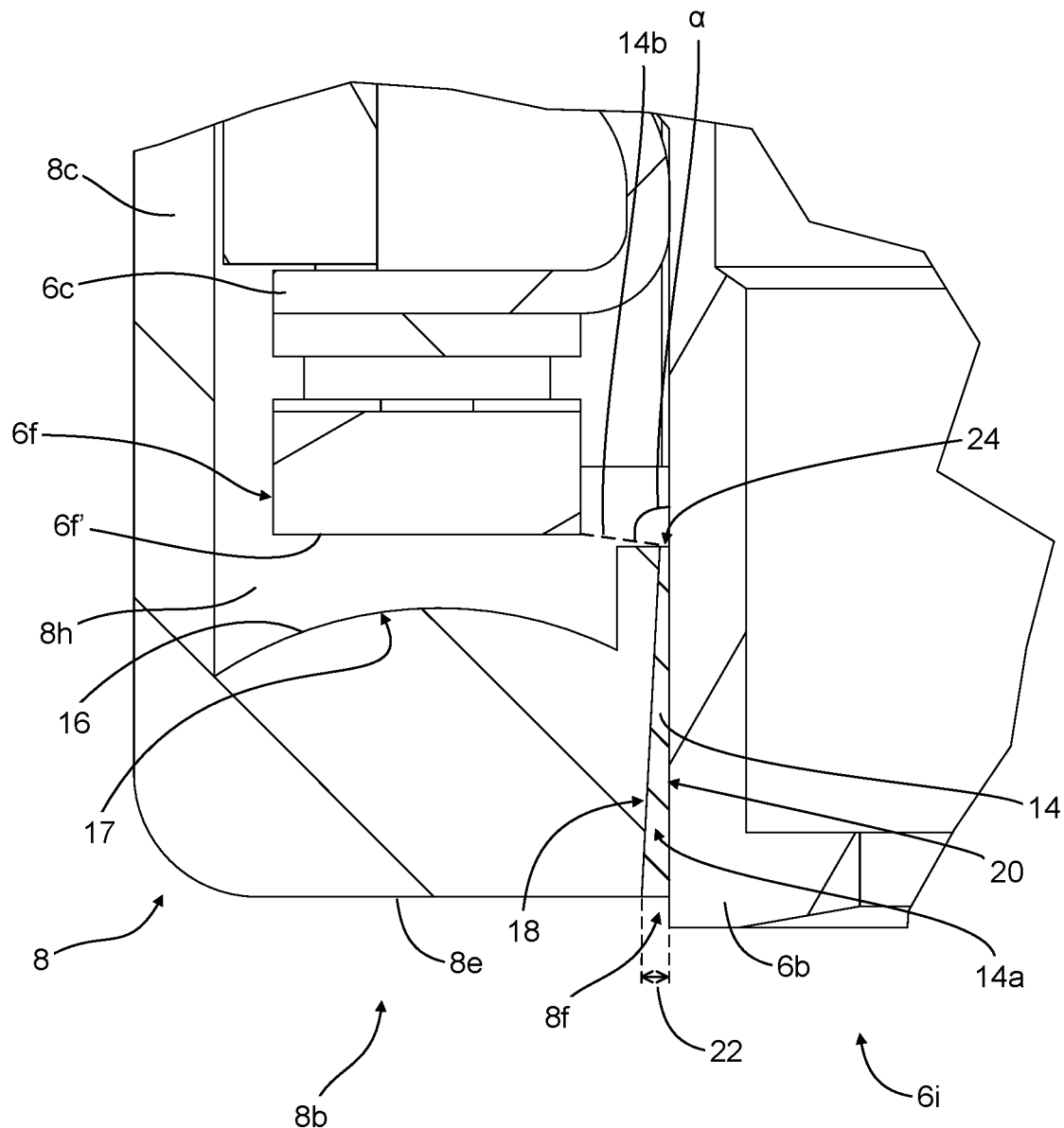
FIG. 6 shows a detail view C of the tip part of FIG. 4b.

Turning to FIG. 6, in order to ensure liquid tightness from the distal end of the exterior housing 8, the exterior housing 8 and the lens barrel 6b is to be sealed. The opening 8f of the distal end wall 8e of the exterior housing 8 is provided so that when the lens barrel 6b is inserted a wedge-shaped axially extending gap or adhesive spacing 14a is formed between the inner surface 18 of the opening 8f and the lens barrel 6b along a circumference or outer surface 20 of the lens barrel 6b. A radial extent of the adhesive spacing 14a is gradually reduced along the proximal-distal direction PD towards the proximal spacing 8h of the exterior housing 8. The radial extent or distance 22 of the adhesive spacing 14a is at least 3 times greater at the distal end than the radial extent or distance 24 at the proximal end. The axial extent of the adhesive spacing 14a is about 40 times greater than the radial extent of the proximal end of the adhesive spacing. In the embodiment shown, the inner surface 18 of the opening 8f and the outer surface 20 of the lens barrel 6b are oriented non-parallel relative to one another. More specifically, the inner surface 18 of the opening 8f is conical and the outer surface 20 of the lens barrel 6b is cylindrical. The lens barrel 6b extends further distally than the distal end wall 6e of the exterior housing 8, so that a distal portion of the lens barrel 6b protrudes from the distal end wall 8e.

The tip part 5 is oriented so that the distal end 6i of the lens barrel 6b and the distal end 6b of the exterior housing are pointing upwardly. In FIG. 6 this corresponds to turning the bottom of the page upwards. An UV-curable adhesive 14 is then injected into the adhesive spacing 14a and is drawn further into the narrow adhesive spacing 14a by capillary action. The adhesive 14 is caused to harden by exposure to UV light and forms an opaque barrier preventing light ingress through the side of the lens barrel 6b. This ensures that the lens barrel 6b is adhered and sealed to the distal end wall 8e of the exterior housing 8.

The adhesive spacing 14a directs the injected adhesive 14 away from the light emitting surface 6f' of the at least one light source 6f by being positioned so that a line 14b between an edge of the light emitting surface 6f closest to the proximal end of the adhesive spacing 14a forms an angle α of about 85° in relation to the proximal-distal axis PD. The line 14b extends uninterrupted in the spacing 8h of the exterior housing 8.

The following is a list of reference numerals used throughout this specification.
1 endoscope
11 monitor
12 cable socket
13 monitor cable
2 handle
21 Control lever
3 insertion tube
3a proximal end
3b distal end
4 bending section
41 distal end segment
41b distal end
41c circumferential side wall
41d spacing
41e opening
41f adhesive injection hole
42 intermediate segment
43 proximal segment
5 tip part
5a proximal end
5b distal end
6 camera assembly
6a image sensor
6b lens barrel
6c printed circuit board
6d Mounting frame
6e cable tube
6f first light source
6f' first light emitting surface
6g second light source
6g' second light emitting surface
6h proximal end
6i distal end
7 steering wire
8 exterior housing
8a proximal end
8b distal end
8c circumferential side wall
8d spacing
8e distal end wall
8f opening
8g proximal spacing
8h distal spacing
9 injection device
9a injection tube
9b control device
10 adhesive
10a level
14 adhesive
14a adhesive spacing
14b line
16 interior surface
17 lens
18 inner surface
20 outer surface
22 distance
24 distance α angle
PD proximal-distal axis

The invention claimed is:

1. A method for manufacture of a tip part for an endoscope, said method comprising:
   providing a camera assembly including an image sensor, a lens barrel positioned at a distal end of the camera assembly, at least one light source with a light emitting surface configured to emit light distally, and a circuit board positioned at a proximal end of the camera assembly;
   providing an exterior housing of the tip part, the exterior housing comprising a circumferential wall and a distal end wall, the circumferential wall and the distal end wall defining an internal volume of the exterior housing, the distal end wall being integral with the circumferential wall and having an opening, the distal end wall including an interior surface configured for transferring light received from the at least one light source therethrough and a proximal portion extending proximally from the interior surface;
   inserting the lens barrel of the camera assembly into the interior volume of the exterior housing so that a distal end of the lens barrel extends into the opening, with the proximal portion extending proximally from the internal surface is adjacent the lens barrel, and so that a gap is provided between the opening and the lens barrel along a periphery of the lens barrel and extending further proximally than the interior surface of the distal wall, the gap further extending between the proximal portion and the periphery of the lens barrel, a radial extent of the gap decreasing in a direction towards the internal volume of the exterior housing;
   injecting an adhesive into the gap, wherein the proximal portion comprises a barrel-facing surface; and
   allowing or causing the adhesive to harden so as to adhere the lens barrel to the distal end wall of the exterior housing, wherein the adhesive adheres the barrel-facing surface of the proximal portion and the periphery of the lens barrel.

2. The method of claim 1, wherein the gap is sized and configured to draw the adhesive into the gap by capillary action.

3. A tip part for an endoscope, comprising:
   a camera assembly comprising an image sensor, a lens barrel positioned at a distal end of the camera assembly, at least one light source with a light emitting surface configured to emit light distally, and a circuit board positioned at a proximal end of the camera assembly;
   an exterior housing comprising a circumferential wall and a distal end wall, the distal end wall being integral with the circumferential wall and having an opening, the circumferential wall and the distal end wall defining an interior volume of the exterior housing, wherein the lens barrel of the camera assembly is positioned within the interior volume of the exterior housing with a distal end of the lens barrel extending into the opening, a gap formed between the opening and the lens barrel along a periphery of the lens barrel, a radial extent of the gap decreasing in a direction towards the interior volume of the exterior housing, and a proximal end of the gap terminating in the interior volume of the exterior housing; and
   a hardened adhesive positioned in the gap and adhering the lens barrel to the distal end wall of the exterior housing,
   wherein the distal end wall includes an interior surface configured for transferring light received from the at least one light source therethrough and a proximal portion extending proximally from the interior surface adjacent to the lens barrel,
   wherein the gap extends further proximally than the interior surface between the proximal portion,. extending proximally from the interior surface, and the lens barrel,
   wherein the proximal portion comprises a barrel-facing surface, and
   wherein the adhesive adheres the barrel-facing surface and the periphery of the lens barrel.

4. The tip part of claim 3, wherein the gap is V-shaped and narrows from a distal end of the gap towards the proximal end of the gap.

5. The tip part of claim 3, wherein the camera assembly further comprises at least one light source with a light emitting surface configured to emit light distally, wherein the proximal end of the gap is substantially aligned with the light emitting surface of the at least one light source.

6. The tip part of claim 4, wherein the radial extent of the gap is at least 1.5 times greater at the distal end than at the proximal end of the gap.

7. The tip part of claim 3, wherein an axial extent of the gap is at least 5 times greater than the radial extent of the gap at the proximal end of the gap.

8. The tip part of claim 3, wherein the lens barrel extends further distally than the distal end wall of the exterior housing.

9. The tip part of claim 3, wherein the hardened adhesive positioned in the gap seals the gap to provide a fluidly sealed distal tip end of the tip part.

10. The tip part of claim 9, further comprising a bending section including a distal end segment, wherein a proximal end of the exterior housing is secured and sealed to the distal end segment of the bending section.

11. An endoscope comprising a tip part according to claim 3, the tip part being positioned at a distal end of the endoscope.

12. A system for visually inspecting inaccessible places such as human body cavities, the system comprising:
   an endoscope according to claim 11 and a monitor, wherein the endoscope is connectable to the monitor, and the monitor is configured to display an image from the camera assembly of the endoscope.

13. The tip part according to claim 3, wherein the distal end wall and the circumferential wall are formed in one-piece.

14. The tip part according to claim 6, wherein the radial extent of the gap is 3 times greater at the distal end than at the proximal end of the gap.

15. The tip part of claim 3, wherein the gap is formed between an inner surface of the opening and an outer surface of the lens barrel, the inner surface of the opening and the outer surface of the lens barrel oriented, in an axial direction, non-parallel relative to one another.

16. The tip part of claim 15, wherein the inner surface of the opening is conically shaped.

17. The tip part of claim 16, wherein the outer surface of the lens barrel is cylindrically shaped.

18. The tip part of claim 3, wherein the lens barrel comprises a proximal portion and a distal portion, the distal portion having a cross-section narrower than the proximal portion, wherein the at least one light source is positioned distally of and at least partially overlapping longitudinally the proximal portion of the lens barrel.

19. The tip part of claim 3, further comprising a mounting frame for the camera assembly, the mounting frame comprising a proximal portion proximal of the image sensor and a distal portion extending distally of the image sensor, and wherein the distal portion comprises a distal surface overlapping and providing backing support for the at least one light source.

20. The tip part of claim 19, wherein the lens barrel comprises a proximal portion and a distal portion, the distal portion having a cross-section narrower than the proximal portion, wherein the distal portion of the mounting frame extends distally of the proximal portion of the lens barrel, wherein the at least one light source is positioned distally of and at least partially overlapping longitudinally the proximal portion of the lens barrel.

* * * * *